(12) United States Patent
Chan et al.

(10) Patent No.: US 11,883,135 B2
(45) Date of Patent: Jan. 30, 2024

(54) WEARABLE THREE-DIMENSIONAL AURICULAR MULTI-POINT BIO-SIGNAL ACQUISITION, HEALTH STATUS MONITORING, AND BIO-STIMULATION DEVICE

(71) Applicant: City University of Hong Kong, Hong Kong (HK)

(72) Inventors: Ho-Yin Chan, Hong Kong (HK); Qing Yun Huang, Hong Kong (HK); Wen Jung Li, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 272 days.

(21) Appl. No.: 17/512,672

(22) Filed: Oct. 28, 2021

(65) Prior Publication Data

US 2023/0138891 A1    May 4, 2023

(51) Int. Cl.
| | |
|---|---|
| *A61B 5/0205* | (2006.01) |
| *A61B 5/00* | (2006.01) |
| *A61B 5/369* | (2021.01) |
| *A61B 5/0531* | (2021.01) |
| *A61B 5/25* | (2021.01) |

(Continued)

(52) U.S. Cl.
CPC ........ *A61B 5/02055* (2013.01); *A61B 5/0002* (2013.01); *A61B 5/0531* (2013.01); *A61B 5/25* (2021.01); *A61B 5/318* (2021.01); *A61B 5/369* (2021.01); *A61B 5/6815* (2013.01);
(Continued)

(58) Field of Classification Search
CPC . A61B 5/02055; A61B 5/0002; A61B 5/0531; A61B 5/25; A61B 5/318; A61B 5/369; A61B 5/6815; A61N 1/36036; B33Y 10/00; B33Y 50/00; B33Y 80/00
See application file for complete search history.

(56) References Cited

U.S. PATENT DOCUMENTS

2013/0301845 A1\* 11/2013 Royal .................... A61H 39/04
                                                        29/729
2013/0331640 A1    12/2013 Nabat et al.
(Continued)

FOREIGN PATENT DOCUMENTS

| | | |
|---|---|---|
| CN | 2159210 Y | 3/1994 |
| CN | 202061250 U | 12/2011 |
| WO | 2019232157 A1 | 12/2019 |

*Primary Examiner* — Jonathan T Kuo
(74) *Attorney, Agent, or Firm* — Idea Intellectual Limited; Margaret A. Burke; Sam T. Yip

(57) ABSTRACT

The present invention provides a personalized, three-dimensional printed, human auricle-specific multiple auricular points' bio-signal acquisition, health status monitoring, and bio-stimulation device, including an artificial ear model made of at least one bio-compatible, flexible polymer, a plurality of sensing and stimulating electrodes with at least one sensing end and a signal acquisition/processing end penetrating through a body of the ear mold conformably with a human auricle so that a surface of the ear mold where sensing end of the electrodes is disposed creates an electrode-human skin interface for bio-signal detection and bio-stimulation responsive thereto. Methods of fabricating the device based on 3-D printing, 3D scanning and modelling techniques and using thereof for bio-signal acquisition, analysis, health status monitoring and bio-stimulation are also provided.

18 Claims, 9 Drawing Sheets

(51) Int. Cl.
*A61N 1/36* (2006.01)
*B33Y 80/00* (2015.01)
*B33Y 50/00* (2015.01)
*B33Y 10/00* (2015.01)
*A61B 5/318* (2021.01)

(52) U.S. Cl.
CPC .......... *A61N 1/36036* (2017.08); *B33Y 10/00* (2014.12); *B33Y 50/00* (2014.12); *B33Y 80/00* (2014.12)

(56) References Cited

U.S. PATENT DOCUMENTS

| | | | |
|---|---|---|---|
| 2020/0016032 A1 | 1/2020 | Frer | |
| 2021/0137785 A1* | 5/2021 | Seo | A61H 9/0078 |
| 2021/0196565 A1* | 7/2021 | Marinakis | A61N 1/36036 |
| 2022/0143390 A1* | 5/2022 | Klein | A61N 1/36036 |

* cited by examiner

FIG. 4E(iii)

140
WEARABLE THREE-DIMENSIONAL AURICULAR MULTI-POINT BIO-SIGNAL ACQUISITION, HEALTH STATUS MONITORING, AND BIO-STIMULATION DEVICE

FIELD OF THE INVENTION

The present invention relates to a wearable three-dimensional auricular multi-point bio-signal acquisition, health status monitoring, and bio-stimulation device. The present invention also relates to a method of making the device by 3-D printing.

BACKGROUND

Intelligent wearable electronics have recently emerged and have attracted considerable attention from researchers with the advancements of material science, fabrication techniques, and data science. Some devices have broad healthcare applications in medical diagnosis and therapy by physiological signal monitoring such as electrocardiography (ECG), electroencephalography (EEG), heart rate, blood pressure, blood oxygen saturation, and body temperature, etc. Most wearable electronics are mounted on the human organs, such as wrists, fingers, head, or legs-etc. However, few of them focus on collecting bio-signals from the entire ear auricles.

Human ears provide diverse physiological signals for health monitoring, such as blood oxygen saturation, pulse, EEG, temperature and etc. Underneath the auricular skin, a complicated network involving branches of nerves and blood vessels is formed across the ear auricle. This special subcutaneous biological structure may provide rich physiological information varying with regions. Currently, doctors primarily use single-probe auricular detector (SPAD) with a single rigid probe as a tool for clinical diagnosis. The SPAD can only detect one point followed by another by moving around the skin surface manually, and is sensitive to pressure variation from the user's hands. Further, most devices only have a sound alarm or a light indicator for reminder of abnormal signal and cannot record data for further analysis. Additionally, such prior art devices cannot provide clear user interface as to real-time signal changes; such signal changes are quite valuable for clinical diagnosis and treatment.

However, most current ear-worn sensing devices with earplug-like or clip-like structures have traditionally focused on collecting data comprising audiology, EEG and blood oxygen saturation at a single location such as ear canal, earlobe, antihelix, etc., but not covering the entire auricle. Thus, only temporal signal recording in a specific region can be acquired and spatial-level characterization is missing. For example, the commercial single-probe auricular detector (SPAD) with a rigid metal probe is primarily used to detect auricular skin conductance levels point by point when manually moving the probe over the skin surface. Here acquired signals are also extremely sensitive to the pressure applied, leading to low measurement repeatability.

Additionally, such prior art devices cannot record data for further analysis and provide clear user interface as to real-time full-auricle signal changes; such signal changes are quite valuable for health status diagnosis and monitoring. Therefore, reliability, coverage, repeatability, quantization and visualization of full-auricle bio-signal measurements have been challenging, and there is a critical need for a conformable auricular sensing device that can achieve multi-point bio-signals acquisition and stimulation across the entire auricle for healthcare applications.

CN2159210Y discloses an ear mold with protrusions corresponding to some auricular acupoints, but it does not have any bio-signal acquisition, processing, analysis, and bio-stimulation functions because it is a non-electrical, non-magnetic, (that is, purely mechanical) device.

CN20206125U discloses a whole ear acupoint-specific electrical acupuncture therapeutic device, but focuses more on the acupoints located in the inner ear, and no geometric designing and locating is provided according to the user's auricle. As a result, there is possibility that some fixed stimulation points on the device do not correspond to the location of the acupoints of certain individuals because the location of those acupoints varies individual-by-individual.

US20130331640A1 discloses an optical therapeutic apparatus to be worn overhead or around a wearer's ear to provide optical stimulation massage to the wearer's ear by projecting laser beam toward the acupuncture points. Again, this apparatus does not have bio-signal acquisition, processing and analysis modules, and also is not custom-made according to individual auricular geometry. Geometrical variation does affect the effect of acupuncture if the device does not correspond to the auricular points of a particular individual.

WO2019232157A1 discloses a device for auricular acupuncture including an ear retention device substantially contacting a patient's auricular surface to allow sufficient energy from either optical or electric source to stimulate corresponding auricular acupuncture sites. Although the system disclosed in this published patent application has some feedback mechanism responsive to the acupuncture stimulation provided by the device, again, this is not a personalized device geometrically conforming with an individual's auricle. Efficiency of bio-stimulation provided by this kind of device varies individual-by-individual, and the reliability or stability of the feedback mechanism provided thereby is doubtful.

US2020016032A1 discloses a device for auriculotherapy including a number of projections which were claimed to engage acupressure points of the ear and fitted to the ear. However, from various embodiments provided in this published application, it is apparent that the location of the projections to individual auricle is not so accurate because there is no disclosure of how to fit individual auricle in terms of the geometric location of auricular points of different individuals.

Therefore, a reliable, repeatable, personalized device with quantitative measurement and visualization capabilities of bio-signals from human auricle is needed.

SUMMARY OF THE INVENTION

To address the aforementioned shortcomings, the present invention provides a three-dimensional printed, personalized auricular multi-point bio-signal acquisition, heath status monitoring, and bio-stimulation device comprising:

an artificial ear model configured to be complementary morphologically to a wearer's outer ear comprising a plurality of 3D printable materials forming a body prepared according to multiple geometrically pre-marked and pre-sampled point locations by 3D scanning, and one or more sensing and simulating electrodes by 3D printing with a bio-signal sensing end exposed on a surface of the artificial ear model that is proximal to a surface of the wearer's outer ear where the majority of auricular points of human body is located;

at least a data acquisition unit for independently and simultaneously collecting real-time bio-signals detected by the plurality of sensing and stimulating electrodes from the auricular points of the wearer's outer ear and processed by an automatic 3D contour mapping user interface.

In one embodiment, the present device further includes a bio-signal processor so that the real-time bio-signals detected by the one or more sensing and stimulating electrodes is/are responded to by the bio-signal processor with a corresponding stimulating response signal being sent from the bio-signal processor to the respective electrode or electrodes in order to stimulate respective auricular point on the wearer's outer ear.

In one embodiment, the bio-signal processor is integral into or external to the body of the artificial ear model.

In one embodiment, the bio-signal processor communicates with the one or more sensing and stimulating electrodes physically or wirelessly.

In one embodiment, the bio-signals include information of physical and physiological signals of the wearer including electrocardiography, electroencephalography, heart rate, blood pressure, blood oxygen saturation, heat stimulation, skin impedance, temperature, hydration, and pressure with respect to the auricular geometry and spatial distribution of auricular points corresponding to the sensing ends of the one or more sensing and stimulating electrodes, such that temporospatial signal distribution on the wearer's outer ear is visualized by the automatic 3D contour mapping user interface.

In one embodiment, the present device further includes a power supply either internal, external, or both to the body of the artificial ear model.

In one embodiment, the body of the artificial ear model further includes a plurality of inner electrode pathways, and the plurality of 3-D printable materials comprises a bio-compatible and flexible polymer, and electrically conductive material for forming the inner electrode pathways and the one or more sensing and stimulating electrodes which is/are partially embedded into the body through the inner electrode pathways.

In one embodiment, the one or more sensing and stimulating electrodes is/are configured to communicate with a plurality of interconnections, and in some embodiments, the one or more sensing and stimulating electrodes may go through the inner electrode pathways to have multiple sensing ends disposed at a surface which is proximal to the surface of the wearer's ear where the majority of the auricular points is located.

In other embodiment, the one or more sensing and stimulating electrodes may be directly integrated on the surface of the body of the ear model, where the body may be shell-like and without any inner electrode pathways.

In one embodiment, the bio-compatible and flexible polymer includes any flexible elastomer.

In one embodiment, the electrically conductive material comprises graphene-enhanced polylactic acid In one embodiment, the present device further includes some functional modules of other sensors, including but not limited to, noise cancelling and/or audio signal processing modules/sensors being optionally integrated into the present device.

A second aspect of the present invention provides a method for making the present device described herein. The method includes:

providing a reverse auricular mold comprising preparing a three-dimensional artificial ear body by 3-D molding to have an ear impression shaping conformably with human auricle, mixing at least one bio-compatible polymer with at least one catalyzer uniformly to obtain a mixture, and filling up the three-dimensional artificial ear body with the mixture until the mixture is solidified in order to form a body of the reverse auricular mold;

scanning a three-dimensional geometry of the human auricle comprising using a structural-light-based three-dimensional scanning to generate a point cloud for subsequent three-dimensional geometrical configuration of the reverse auricular mold;

subjecting the reverse auricular mold simultaneously to a 3-D printing device incorporating at least a flexible elastomer and a conductive material so as to generate one or more sensing and stimulating electrodes with a sensing end of each of the electrodes that is exposed at the surface which is proximal to the surface of the wearer's outer ear where the majority of the auricular points is located such that a mechanically stable whilst flexible electrode-human skin interface is formed, and optionally also to fill up a cavity of the reverse auricular mold (if the body is shell-like) to form a flexible body of the present device. Alternatively, the body can be a solid without any cavity.

In one embodiment, the method of the second aspect further includes incorporating a bio-signal processor, a signal transceiver and a power supply into the body of the reverse auricular mold to receive and process the bio-signals detected by one or more sensing and stimulating electrodes through a plurality of inner electrode pathways and a plurality of interconnections, and transmit the processed bio-signals to an automatic 3D contour mapping user interface either physically or remotely communicated with said device.

In one embodiment, the bio-signals comprise information of physical and physiological signals of the wearer including electrocardiography, electroencephalography, heart rate, blood pressure, blood oxygen saturation, heat stimulation, skin impedance, temperature, hydration, and pressure with respect to auricular geometry and spatial distribution of auricular points of the wearer's outer ear corresponding to the sensing ends of the one or more sensing and stimulating electrodes, such that temporospatial signal distribution on the wearer's outer ear is visualized by the automatic 3D contour mapping user interface.

A third aspect of the present invention provides a method for diagnosing and/or monitoring health status of a subject comprising providing the device described herein to the subject by physically or non-physically contacting a surface of a body of said device with a surface of an outer ear of the subject, the surface of the body of said device which is in physical or non-physical contact with the surface of the outer ear of the subject comprising a plurality of sensing ends of multiple sensing and stimulating electrodes interconnecting with a plurality of interconnections disposed at an opposite side to said surface of the body of the device, said surface of the body of the device forming a mechanically stable whilst flexible electrode-skin interface with the surface of the outer ear of the subject where the majority of auricular points is located in order to receive real-time bio-signals from the surface of the outer ear of the subject and respond to the received bio-signals after being processed and subsequently analyzed by an automatic 3D contour mapping user interface.

In one embodiment, the bio-signals comprise information of physical and physiological signals of the wearer including electrocardiography, electroencephalography, heart rate, blood pressure, blood oxygen saturation, -heat stimulation, skin impedance, temperature, hydration, and pressure with respect to auricular geometry and spatial distribution of auricular points of the subject's outer ear corresponding to the sensing ends of the one or more sensing and stimulating electrodes, such that temporospatial signal distribution on the subject's outer ear is visualized by the automatic 3D contour mapping user interface.

In one embodiment, the automatic 3D contour mapping user interface, after analyzing the bio-signals processed and transmitted from a bio-signal processor and transceiver of the device, gives instruction to the device to generate and send one or more signals, including but not limited to, electrical, magnetic, and/or mechanical stimulating signal(s), through the one or more sensing and stimulating electrodes to one or more of the corresponding auricular points on the subject's outer ear to stimulate thereof in order to respond to the corresponding health conditions or symptoms that are reflected by the bio-signals.

In one embodiment, the bio-signals received by the one or more sensing and stimulating electrodes are normalized by the bio-signal processor prior to being analyzed by the automatic 3D contour mapping user interface.

It should be understood that the present invention is not limited to a device for a fixed type of bio-signal sensing at multiple auricular points, but should also include any wearable ear sensors such as ear sensors having function of collecting multiple bio-signals including EEG, $SpO_2$, blood pressure, etc., for human being.

BRIEF DESCRIPTION OF THE DRAWINGS

Embodiments of the invention are described in more details hereinafter with reference to the drawings, in which.

DETAILED DESCRIPTION OF THE INVENTION

In the following description, the present device, methods of fabrication and using thereof for detecting, measuring, analyzing and responding to the bio-signals from human auricular points, and the like are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

It should be apparent to practitioner skilled in the art that the foregoing examples are only for the purposes of illustration of working principle of the present invention. It is not intended to be exhaustive or to limit the invention to the precise forms disclosed.

1. Preparation of Reverse Auricular Mold (RAM)

Figure 1A:
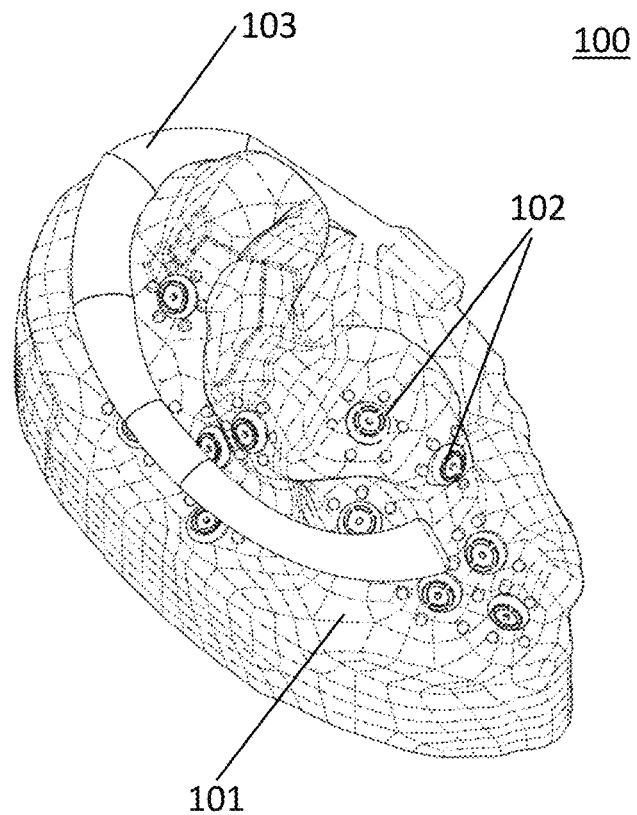
FIG. 1A schematically depicts the present device from a front perspective view according to an embodiment of the present invention.
Figure 1B:
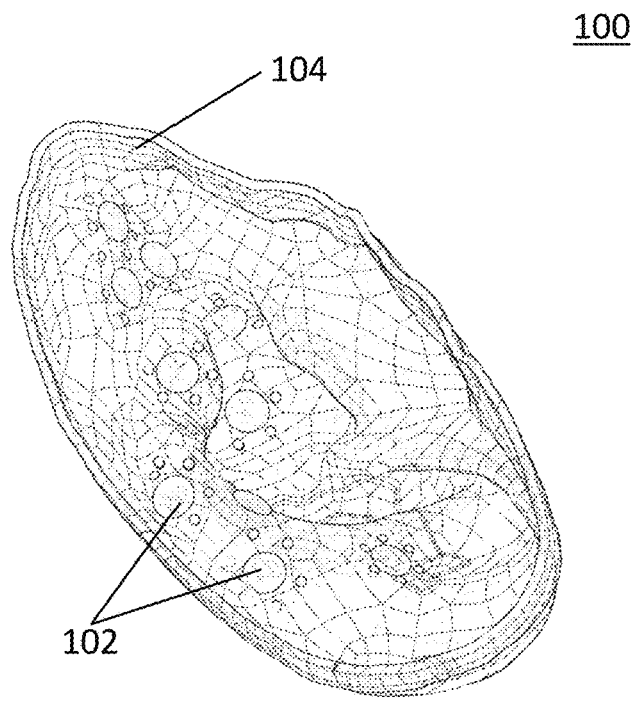
FIG. 1B schematically depicts the present device from a rear perspective view according to an embodiment of the present invention.
Figure 6:
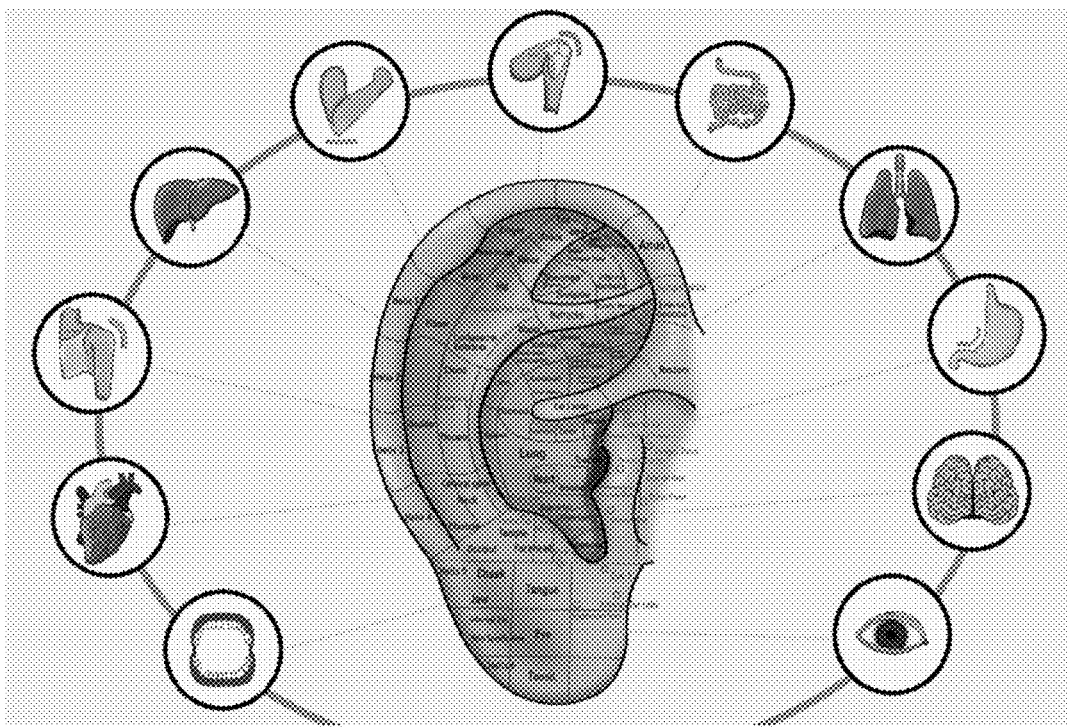
FIG. 6 is a schematic diagram showing the relationship between each of the auricular points on human auricle and the corresponding body part/organ/tissue according to an embodiment of the present invention.

Turning to FIGS. 1A and 1B, a basic geometric structure of a preferred embodiment of the present device 100 is provided from its front and rear perspective views, respectively. The present device in this example includes a body 101, a plurality of sensing and stimulating electrodes 102 partially embedded into the body 101 of the present device through some electrode pathways (FIGS. 1A and 1B show a state where the electrodes have already been embedded), where each of them has a sensing end (also serves as stimulating end) being exposed out of the body of the present device to be in contact with a surface of a wearer's auricle (outer ear) where the majority of the auricular points (FIG. 6) is located. Each of the sensing and stimulating electrodes 102 includes a plurality of sub-electrodes 102a (FIG. 2A) for various signals detection or stimulation which are different from that of central electrodes. Alternatively, the sensing and stimulating electrodes according to certain embodiments of the present invention can have protrusions on both ends (and with different levels of heights from at least 0). The present device 100 also includes an ear-anchoring element 103 and a cavity 104 at a rear side of the present device which is distal to the wearer's ear where the majority of the auricular points are located. In other embodiment, the cavity can be absent in the case where the body is a solid.

Figure 2A:
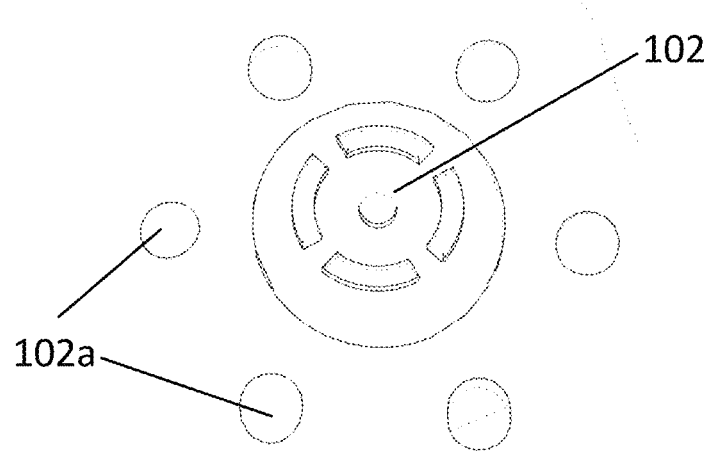
FIG. 2A schematically depicts one of the sensing and stimulating electrodes of the present device according to an embodiment of the present invention.

As shown in FIG. 2A, the sensing end of the sensing and stimulating electrodes 102 is configured to have a plurality of protrusions extending out of the body of the present device and the overall surface of the present device proximal to the surface of the wearer's outer ear is substantially convex relative to the surface of its opposite side where it is substantially flat or even concave. The configuration of having the plurality of protrusions at the sensing end of the sensing and stimulating electrodes 102 increases the contact surface area of the electrodes with the skin of the wearer's auricle such that an electrode-human skin interface is formed between the device and the human auricle. The electrodes are spatially distributed throughout the body of the present device and the location thereof may be determined by a 3-D scan of a reverse auricular mold (RAM) by a structural-light-based scanner or by location directly on the RAM geometry, which will be described in more detail in the subsequent examples/accompanying drawings. In general, there is neither a specific number nor particularly required size of the electrodes in the present device, which may vary (can be scaled up or down) depending on the user/wearer's demand. In certain embodiments, one or more functional materials can be incorporated into the sensing and stimulating electrodes so as to sense or detect physical and/or physiological signals in addition to the bio-signals directly in relation to health status of the wearer. Examples of sensors formed by the one or more functional materials include but are not limited to skin impendence sensors, pressure sensors, hydration sensors, temperature sensors, electrochemical sensors. In a preferred embodiment, the electrodes can serve as both sensing and stimulating elements of the device without interference; the electrodes are configured to be operable as both electrical, magnetic and mechanical stimulators, i.e., capable of providing electrical stimulation, magnetic stimulation and mechanical stimulation in each of the electrodes. The working mode and/or intensity of one electrode can be the same or different from that/those of the other electrodes among the plurality of the sensing and stimulating electrodes.

Figure 2B:
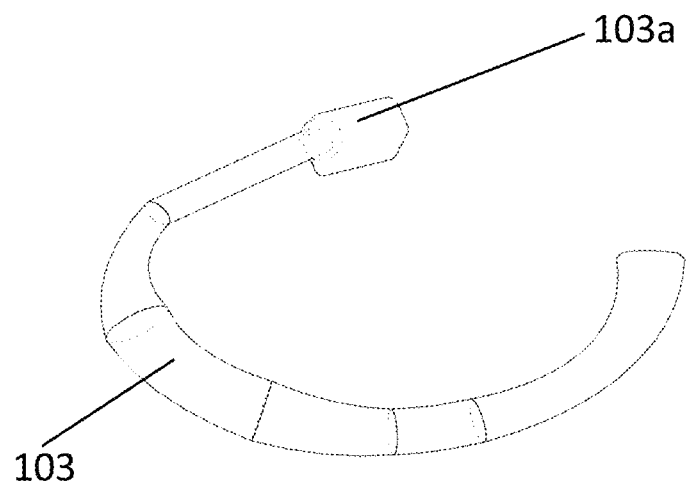
FIG. 2B schematically depicts an ear-anchoring element of the present device according to an embodiment of the present invention.

As shown in FIG. 1A, the ear-anchoring element 103 is incorporated into the device for assisting in anchoring of the device to the human auricle, where it includes a rotation mechanism about a center 103a which is fixed with the body of the present device for re-adjustment of the anchoring position of the device to the wearer's auricle when needed (FIG. 2B). In other embodiments, ear-anchoring element can be absent or substituted with other mechanism to assist anchoring of the device to wearer's auricle.

Figure 3:
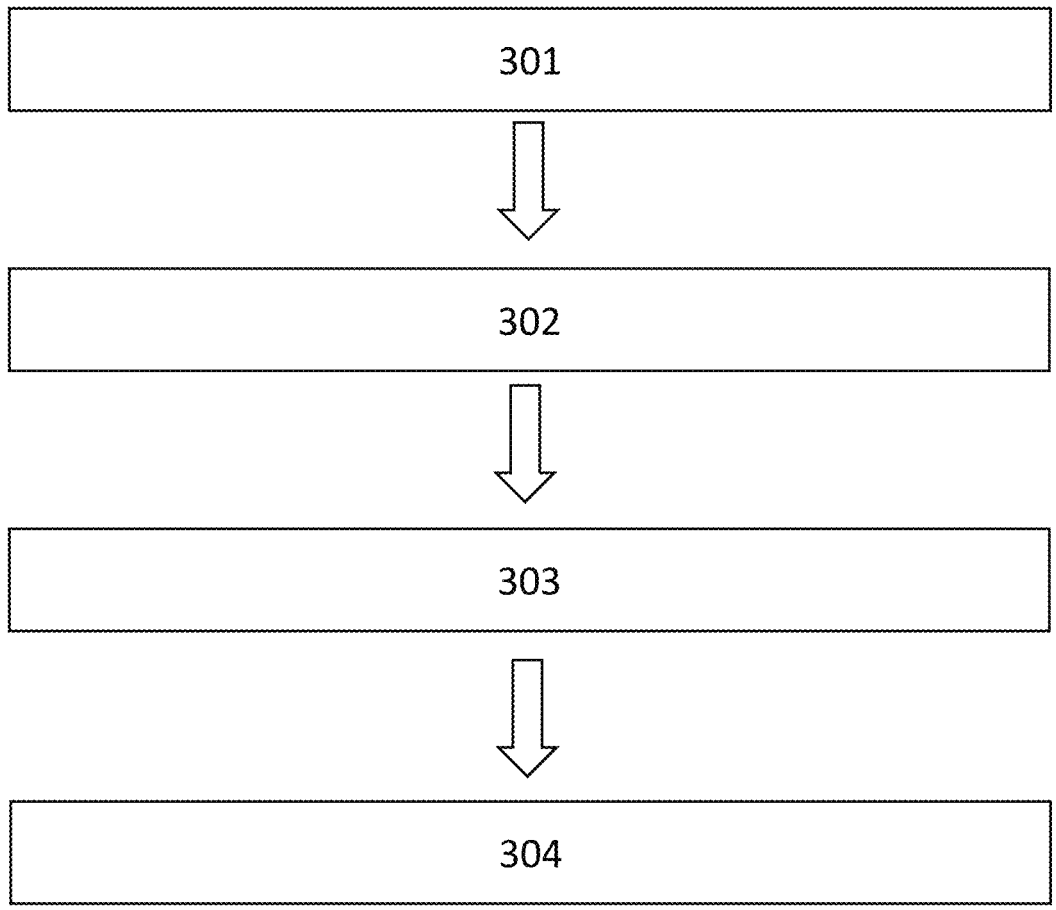
FIG. 3 is a simplified flow chart depicting a method of making the present device according to an embodiment of the present invention.

FIG. 3 presents an overview of the fabrication techniques for the present device. Initially, a three-dimensional ear impression mold conforming with an auricle-specific complex geometry of a wearer is obtained (301). Secondly, a three-dimensional geometric shape of the ear mold is scanned by a 3-D scanner (302) such as a structural-light-based scanner. Thirdly, a plurality of sensing and stimulating electrodes is incorporated into the ear mold by 3-D printing technique (303), e.g., using a 3-D printing device with a 3-D modelling software to print the conductive materials into a plurality of inner electrode pathways of the ear mold. Lastly, one or more functional elements are integrated into the electrodes to render them functional (304), e.g., capable of sensing different physical and/or physiological signals of the wearer.

The ear mold can also be a shell-like structure or a solid without any cavity (not shown in any figures) by 3-D printing which integrates multiple electrodes on the surface thereof, and in such an embodiment, no inner electrode pathways are required.

Figure 4A:
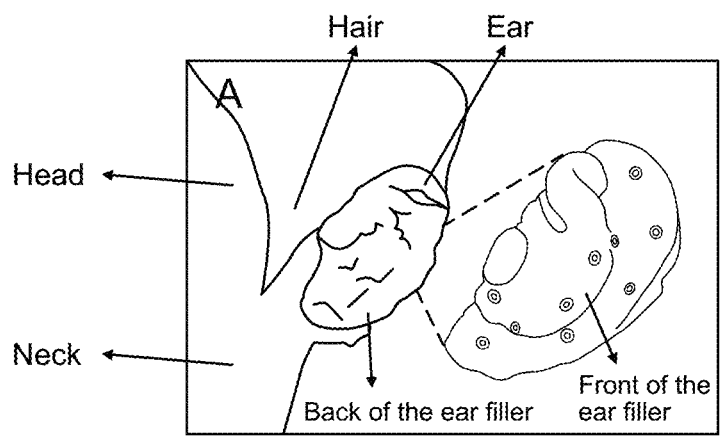
FIG. 4A illustrates the step of ear impression molding corresponding to step 301 in FIG. 3.
Figure 4B:
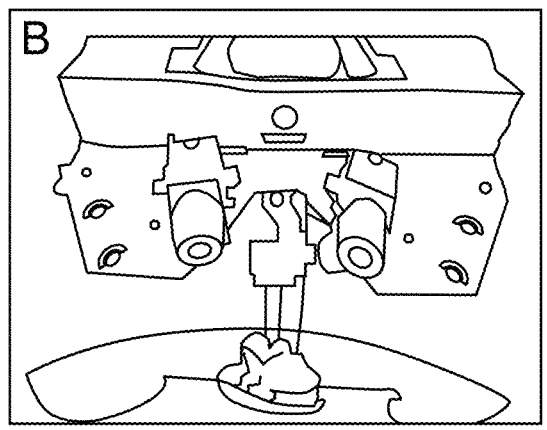
FIGS. 4B and 4C illustrate the step of 3D scanning corresponding to step 302 in FIG. 3.
Figure 4C:
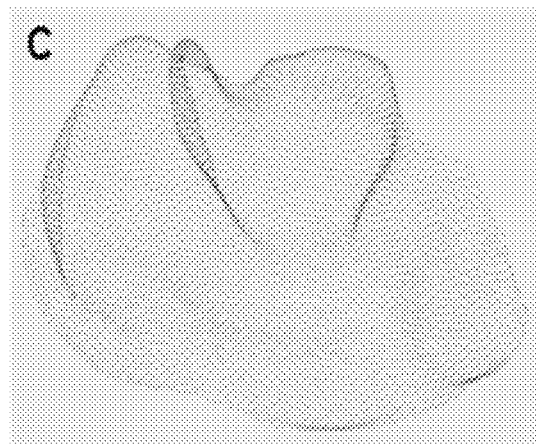
Figure 4D:
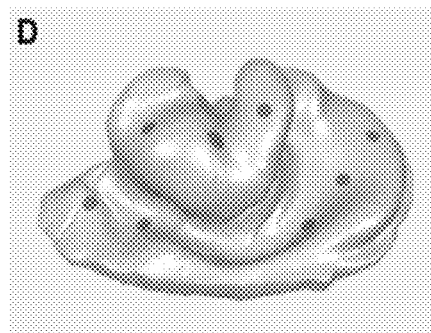
FIG. 4D illustrates electrodes locating and mechanical designing corresponding to step 303 in FIG. 3.

FIGS. 4A-4F further illustrate how the ear mold is fabricated according to certain embodiments of the present invention: FIG. 4A represents ear impression molding. One of the examples of the bio-compatible polymer to make the ear impression mold may be selected from any eco-friendly elastomer commercially available from DETAX GmbH & Co. KG; FIGS. 4B and 4C represent 3D scanning; FIG. 4D represents electrodes locating and mechanical designing (electrodes integrated inside sensor body or along sensor surface).

Figure 4E:
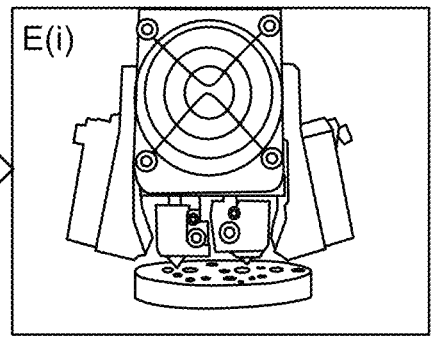
FIG. 4E(i)-(iv) illustrate multi-material 3D printing step corresponding to step 304 in FIG. 3.

FIG. 4E(i) to FIG. 4E(iv) illustrate multi-material 3D printing procedures. The elastomer used in the present device is preferably a 3D-printable, bio-compatible, and flexible polymer such as any flexible elastomer. Additionally, the top region above each of the sensing and stimulating electrodes is filled with softer functional materials which deliver mechanically stable skin-electrode contact. Further, an ear-hook-like fixture is used to assist anchoring the device to the wearer's ear, and an electrical control unit cooperates with the device to measure or apply signals on different points with multiple channels; a friendly user interface is also set up to help visualize the measurement results.

Figure 4F:
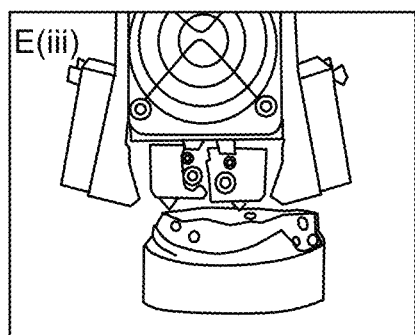
FIG. 4F is an image of an example of the present device connected with an electrical circuit.
Figure 4F:
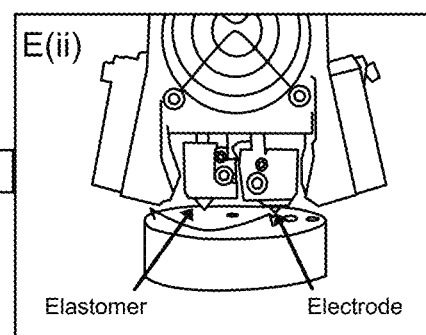
Figure 4F:
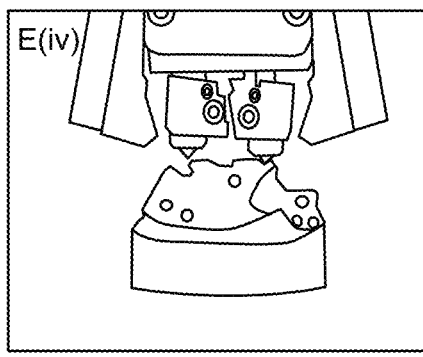
Figure 4F:
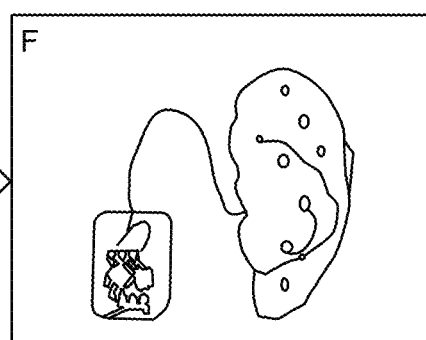

FIG. 4F shows an example of the present device formed by the 3-D printing technique as described herein. As shown in FIG. 4F, the prototype is physically connected with the electric control unit to receive, process, and send to a platform with a user-friendly interface (e.g., a mobile phone or a tablet) in real-time the device signals; the interface can have geometrically marked the sampled point locations and highlight one or more of those with specific values for reference.

It should be understood that sensor used in the present invention can be fabricated by FDM-based 3D-printing technology or any other multi-material fabrication method depending on the demand.

It is also noted that ear impression mold can be fabricated by using any medical-level material; any electrodes by 3D-printing can be fabricated by any type of conductive and printable materials, including but not limited to, graphene-enhanced polylactic acid; sensor body of the present invention can be fabricated by 3D-printing of any soft and printable materials, including but not limited to, thermoplastic elastomer to provide support for the electrodes.

The conductive materials used in the present invention for 3-D printing can not only be used to prepare sensing and stimulating electrodes, but can also be used to integrate with an electrical control unit (not shown in any figures), for example, at the bottom flat surface of the present device or inside the body of the device.

It is further noted that the contact between the present device and the outer ear of the wearer can be dry- or wet-contact, subject to said bio-signal sensing and/or stimulating requirements. Alternatively, the present device can receive bio-signals from and provide stimuli to the wearer's auricular points without physical contact.

2—Data Acquisition and Analysis Tests on Human Subject

Figure 5A:
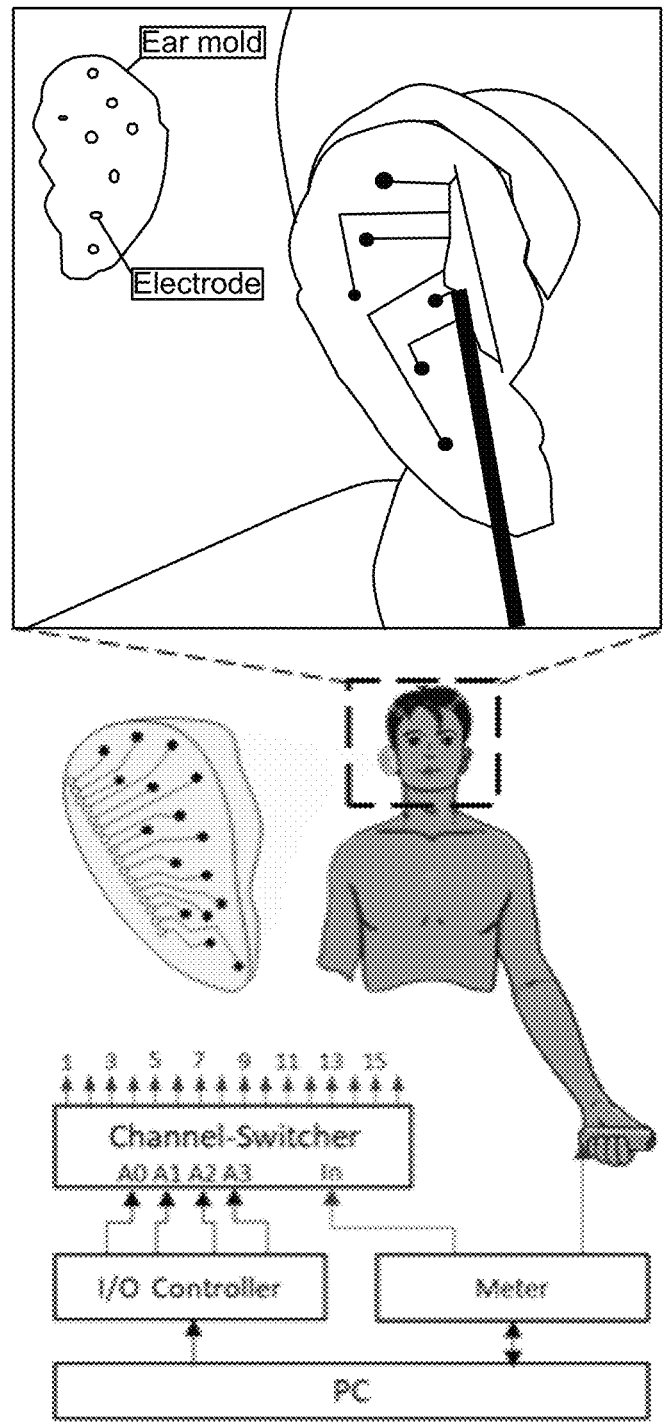
FIG. 5A is a combined image of an example of the present device (from a front and rear views) with a schematic diagram and a flowchart depicting how bio-signals are received and measured from multiple auricular points of a human auricle according to an embodiment of the present invention.
Figure 5B:
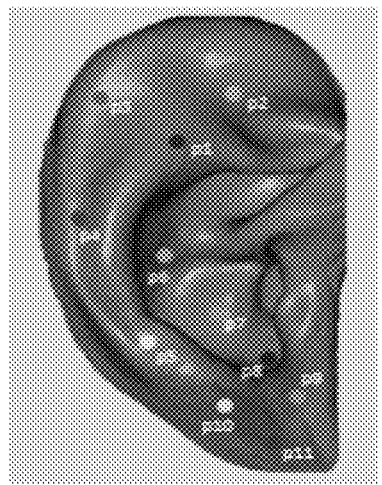
FIG. 5B schematically depicts location of auricular points to be detected with bio-signals by the present device according to an embodiment of the present invention.
Figure 5C:
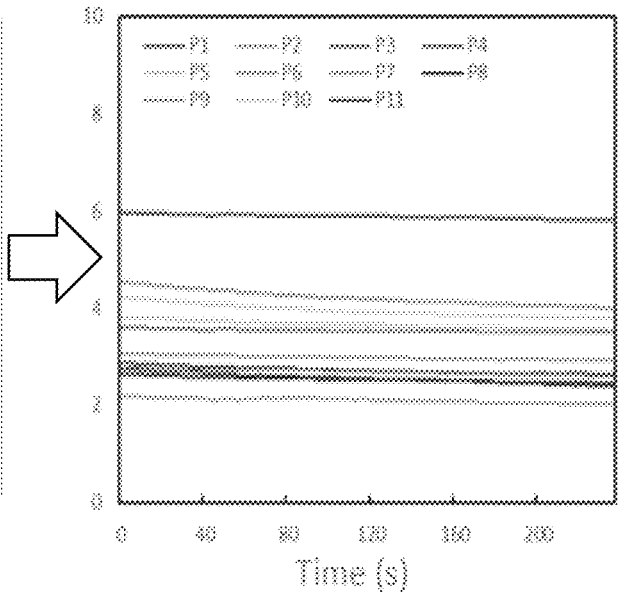
FIG. 5C shows bio-signals detected/measured at multiple auricular points on human auricle by the present device over time according to the embodiment as shown in FIG. 5B.
Figure 5E:
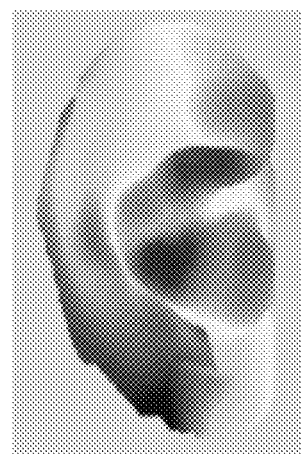
FIG. 5E show a 3-D signal contour by visualization after normalization of the triplicates of signals detected/measured across multiple auricular points on the human auricle according to the embodiments shown in FIGS. 5C and 5D.
Figure 5D:
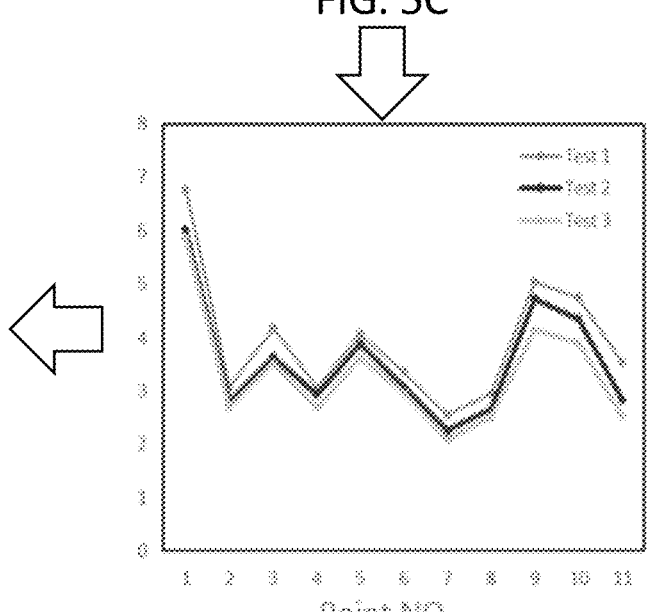
FIG. 5D shows repeatable signal distribution across multiple auricular points on a human auricle in triplicates at each of the auricular points.
Figure 5F:
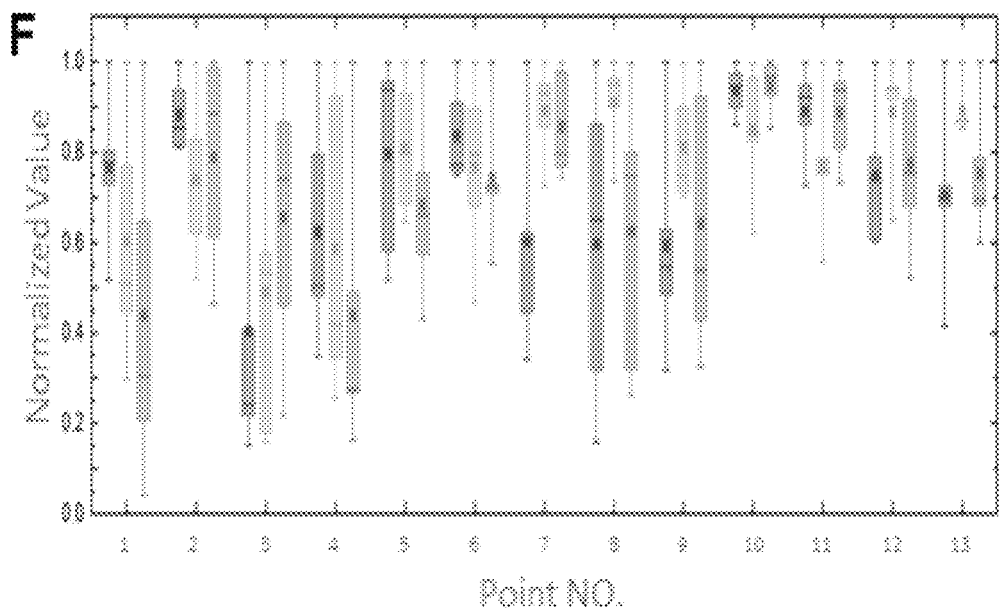
FIG. 5F shows the normalized value of the signals detected/measured at multiple auricular points on the human auricle by a conventional single-probe auricular detector (SPAD)
Figure 5G:
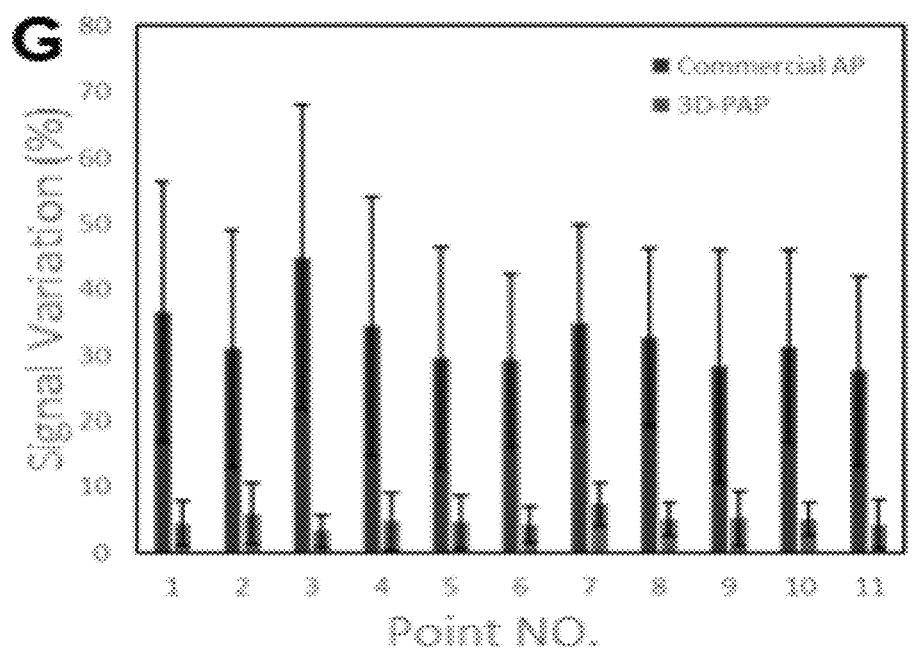
FIG. 5G shows a comparison between a conventional single-probe auricular detector (SPAD) and the present device (3D-PAP) in terms of variation of signals detected/measured at the same multiple auricular points on the human auricle.

One of the applications of the visualized bio-signal monitoring is to help users of the interface including doctors and other medical practitioners, to systematically identify any abnormal patient case and advance auricular diagnosis. In this example, auricular bio-signal measurement was conducted on a number of participants with the prototype obtained according to the description above, which was conducted in accordance with the corresponding ethical guidelines. To standardize the test parameters, all measurements were conducted at the site with no more than 10% temperature and humidity variations which were recorded by commercial meters. Before each measurement, skin surface treatments were applied to remove surface oils and other impurities. Sampled points are spatially distributed across the entire outer ear (FIG. 5B), where signals are recorded; the signals are observed to be stable with a drop (FIG. 5C). Signal variation across all measured points is then characterized with a trend line (FIG. 5D). Based on the discrete raw data, a 3-D contour with both geometric and spatiotemporal signal information is firstly built to visually show the overall signal distribution across the entire auricle (FIG. 5E). Preliminary studies on human subjects were conducted with repeated single-tests for each ear. Benefiting from geometrically designed 3D structure and materials integration, the present device (3D-PAS) can be worn in a mechanically stable manner including a flexible sensor-skin interface to achieve good measurement repeatability. Comparatively, significant data variation occurs in conventional single-probe auricular detector (SPAD) operation (FIG. 5F). Overall, the average variation of each sampled point by both 3D-PAS and commercial AP is compared in FIG. 5G. A universal methodological route for 3-D auricular bio-signal mapping is delivered by the present approach, and higher electrode density driven by user demand can be scaled up to provide various data resolution.

Figure 7:
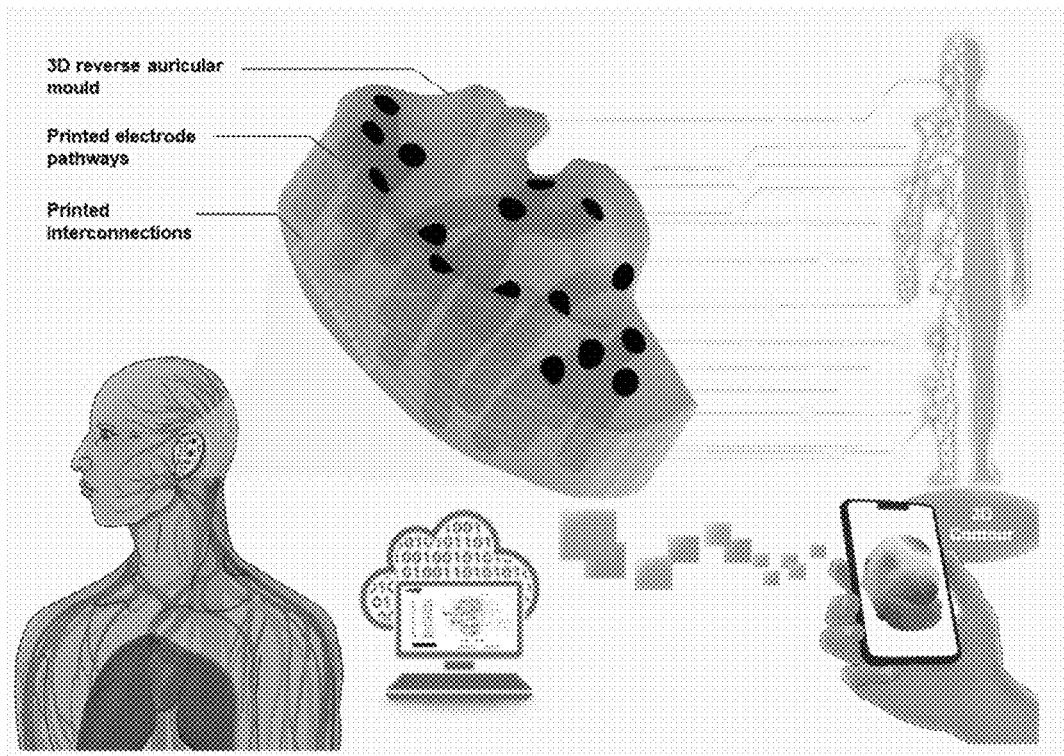
FIG. 7 schematically depicts an overall layout of bio-signal detection, measurement, analysis and response acting on human auricular points by the present device and method according to various embodiments of the present invention.

FIG. 7 shows an overview of the present invention to achieve a multi-functional, three-dimensional auricular points' bio-signal-based device with signal sensing, acquisition, processing, analysis, mapping, health status monitoring, and human auricle-specific electrical and mechanical stimulation functions.

Alternatively, the bio-signals by the sensing and stimulating electrodes of the present invention from the wearer's ear can be acquired through certain contactless sensing mechanisms, including but not limited to, ultra-sonic, optical, etc. (in case of obtaining bio-signals such as pulse, blood pressure, blood oxygen saturation, PPG, etc.)

It is additionally noted that 3D interpolation methods can be alternatively used to generate 3D contour based on said bio-signals acquired from multiple auricular points by the present device.

For auricular imaging, the present invention is not only limited to acquire bio-signals of auricular points simultaneously, but also observe/monitor bio-information under auricular skin tissue, where the bio-information includes but not limited to flow of red blood cells inside the blood vessels underneath wearer's skin, etc.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

INDUSTRIAL APPLICABILITY

The present invention provides a device useful in diagnosis, healthcare monitoring, and personalized medicine; the device provides user comfort while being mechanically stable and quantitatively more reliable and accurate in terms of the bio-signals received as compared to conventional single-probe auricular detector. The present invention is both portable and able to be integrated into any conventional hearing aid or auricular device.

The invention claimed is:

1. A three-dimensional printed, personalized auricular multi- point bio-signal acquisition, heath status monitoring, and bio-stimulation device comprising:
    an artificial ear model configured to be complementary morphologically to a wearer's outer ear comprising a plurality of 3D printable materials forming a body prepared according to multiple geometrically pre-marked and pre-sampled point locations by 3D scanning, and one or more sensing and simulating electrodes by 3D printing with a plurality of bio-signal sensing ends that are exposed on a surface of the artificial ear model that is proximal to a surface of the wearer's outer ear where the majority of auricular points of human body is located;
    at least a data acquisition unit for independently and simultaneously collecting real-time bio-signals detected by the plurality of sensing and stimulating electrodes from the multiple auricular points of the wearer's outer ear and processed by an automatic 3D contour mapping user interface.

2. The device of claim 1, further comprising a bio-signal processor so that the real-time bio-signals detected by the one or more sensing and stimulating electrodes are responded to by a corresponding stimulating response signal being sent from the bio-signal processor to the respective electrode or electrodes in order to stimulate respective auricular point(s) on the wearer's outer ear.

3. The device of claim 2, wherein the bio-signal processor is integral into or external to the body of the artificial ear model.

4. The device of claim 2, wherein the bio-signal processor communicates with the one or more sensing and stimulating electrodes physically or wirelessly.

5. The device of claim 1, wherein the bio-signals comprise information of physical and physiological signals of the wearer including electrocardiography, electroencephalography, heart rate, blood pressure, blood oxygen saturation, stimulation, skin impedance, temperature, hydration, and pressure with respect to the auricular geometry and spatial distribution of multiple auricular points corresponding to the sensing ends of the one or more sensing and stimulating electrodes, such that temporospatial signal distribution on the wearer's outer ear is visualized by the automatic 3D contour mapping user interface.

6. The device of claim 1, further comprising a power supply either internal, external, or both to the body of the artificial ear model.

7. The device of claim 1, wherein the plurality of 3D printable materials comprises a bio-compatible and flexible polymer, and electrically conductive material for forming a plurality of inner electrode pathways, the one or more sensing and stimulating electrodes, and/or integrating with an electrical control unit disposed at a distal surface of the body of the artificial ear model with respect to the wearer's ear.

8. The device of claim 7, wherein the bio-compatible and flexible polymer comprises flexible elastomer.

9. The device of claim 7, wherein the electrically conductive material comprises graphene-enhanced polylactic acid.

10. The device of claim 1, wherein the one or more sensing and stimulating electrodes is/are configured to communicate with a plurality of interconnections through a plurality of inner electrode pathways.

11. A method for making the device of claim 1, the method comprising:
providing a reverse auricular mold comprising preparing a three-dimensional artificial ear body by 3D molding to have an ear impression shaping conformably with human auricle, mixing at least one bio-compatible polymer with at least one catalyzer uniformly to obtain a mixture, and filling up the three-dimensional artificial ear body with the mixture until the mixture is solidified in order to form a body of the reverse auricular mold;
scanning a three-dimensional geometry of the human auricle comprising using a structural-light-based three-dimensional scanning to generate a point cloud for subsequent three-dimensional geometrical configuration of the reverse auricular mold;
subjecting the reverse auricular mold simultaneously to a 3D printing device incorporating at least a flexible elastomer and a conductive material so as to generate one or more sensing and stimulating electrodes with a sensing end of each of the one or more electrodes that is exposed at the surface which is proximal to the surface of the wearer's outer ear where the majority of the auricular points is located such that a mechanically stable whilst flexible electrode-human skin interface is formed.

12. The method of claim 11, further comprising incorporating a bio-signal processor, a signal transceiver and a power supply into the body of the reverse auricular mold to receive and process the bio-signals detected by the one or more sensing and stimulating electrodes and the plurality of interconnections, and transmit the processed bio-signals to an automatic 3D contour mapping user interface either physically or remotely communicated with said device.

13. The method of claim 12, wherein the bio-signals comprise information of physical and physiological signals of the wearer including electrocardiography, electroencephalography, heart rate, blood pressure, blood oxygen saturation, heat stimulation, skin impedance, temperature, hydration, and pressure with respect to auricular geometry and spatial distribution of auricular points of the wearer's outer ear corresponding to the sensing ends of the plurality of sensing and stimulating electrodes, such that temporospatial signal distribution on the wearer's outer ear is visualized by the automatic 3D contour mapping user interface.

14. The method of claim 11, further providing a plurality of inner electrode pathways in the three-dimensional artificial ear body which communicates with a plurality of interconnections being disposed on an opposite side of the reverse auricular mold which is distal to a surface of the wearer's outer ear where the majority of auricular points is located.

15. A method for diagnosing and/or monitoring health status of a subject comprising providing the device of claim 1 to the subject by physically or non-physically contacting a surface of a body of said device with a surface of an outer ear of the subject, the surface of the body of said device which is in physical or non-physical contact with the surface of the outer ear of the subject comprising a plurality of sensing ends of multiple sensing and stimulating electrodes and interconnecting with a plurality of interconnections disposed at an opposite side to said surface of the body of the device, said surface of the body of the device forming a mechanically stable whilst flexible electrode-skin interface with the surface of the outer ear of the subject where the majority of auricular points is located in order to receive real-time bio-signals from the surface of the outer ear of the subject and respond to the received bio-signals after being processed and subsequently analyzed by an automatic 3D contour mapping user interface.

16. The method of claim 15, wherein the bio-signals comprise information of physical and physiological signals of the wearer including electrocardiography, electroencephalography, heart rate, blood pressure, blood oxygen saturation, heat stimulation, skin impedance, temperature, hydration, and pressure with respect to auricular geometry and spatial distribution of auricular points of the subject's outer ear corresponding to the sensing ends of the plurality of sensing and stimulating electrodes, such that temporospatial signal distribution on the subject's outer ear is visualized by the automatic 3D contour mapping user interface.

17. The method of claim 15, wherein the automatic 3D contour mapping user interface, after analyzing the bio-signals processed and transmitted from a bio-signal processor and transceiver of the device, gives instruction to the device to generate and send one or more pulses through the one or more sensing and stimulating electrodes to one or more of the corresponding auricular points on the subject's outer ear to stimulate thereof in order to respond to the corresponding health conditions or symptoms that are reflected by the bio-signals.

18. The method of claim 17, wherein the bio-signals received by the one or more sensing and stimulating electrodes are normalized by the bio-signal processor prior to being analyzed by the automatic 3D contour mapping user interface.

* * * * *